United States Patent
Korfhage et al.

(10) Patent No.: US 10,087,482 B2
(45) Date of Patent: Oct. 2, 2018

(54) AMPLIFICATION OF BISULFITE-REACTED NUCLEIC ACIDS

(75) Inventors: Christian Korfhage, Hilden (DE); Dirk Loeffert, Hilden (DE); Ralf Peist, Hilden (DE); Nicolas Rudinger, Duesseldorf (DE)

(73) Assignee: QIAGEN GMBH, Hilden (DE)

( * ) Notice: Subject to any disclaimer, the term of this patent is extended or adjusted under 35 U.S.C. 154(b) by 834 days.

(21) Appl. No.: 12/865,541

(22) PCT Filed: Feb. 6, 2009

(86) PCT No.: PCT/EP2009/051388
§ 371 (c)(1),
(2), (4) Date: Nov. 1, 2010

(87) PCT Pub. No.: WO2009/098298
PCT Pub. Date: Aug. 13, 2009

(65) Prior Publication Data
US 2011/0045542 A1    Feb. 24, 2011

(30) Foreign Application Priority Data

Feb. 7, 2008    (DE) .................. 10 2008 008 313

(51) Int. Cl.
*C12Q 1/68*    (2018.01)
*C12Q 1/6844*    (2018.01)

(52) U.S. Cl.
CPC .................. *C12Q 1/6844* (2013.01)

(58) Field of Classification Search
None
See application file for complete search history.

(56) References Cited

U.S. PATENT DOCUMENTS

| | | | | |
|---|---|---|---|---|
| 2004/0023207 | A1* | 2/2004 | Polansky | 435/5 |
| 2005/0037393 | A1* | 2/2005 | Gunderson et al. | 435/6 |
| 2006/0263779 | A1* | 11/2006 | Berlin | 435/6 |

FOREIGN PATENT DOCUMENTS

| | | |
|---|---|---|
| WO | WO0070090 | 11/2000 |
| WO | WO2004067775 | 8/2004 |

OTHER PUBLICATIONS

Steward et al. "Measuring Changes in Chromatin Using Micrococcal Nuclease" in Epigenetics Protocols, Methods in Molecular Biology vol. 287, pp. 65-75, edited by T.O. Tollefsbol, Humana Press Inc, Totowa, NJ (2004).*
GenBank GI:23506228 [online] Oct. 6, 2002 [retrieved on Jan. 6, 2013] retrieved from http://www.ncbi.nlm.nih.gov/nuccore/af453522.*
Nakayama et al. GSTP1 CpG Island Hypermethylation as a Molecular Biomarker for Prostate Cancer. Journal of Cellular Biochemistry 91:540-552 (2004).*
Dean et al. Comprehensive human genome amplification usingmultiple displacement amplification. PNAS 99(8):5261-5266 (2002).*
Chen & Herbert. Directed termination of the polymerase chain reaction: Kinetics and applications in mutation detection. Genome 42(1):72-79 (1999).*
Beier et al. Monitoring methylation changes in cancer. Adv Biochem Engin/Biotechnol 104:1-11 (2007).*
Davis et al. On the relationship between GC content and the number of predicted microRNA binding sites my MicroInspector. Computational biology and chemistry 32:222-226 (2008).*
Pepin et al. Rapid and sensitive detection of ostreid herpesvirus 1 in oyster samples by real-time PCR. Journal of Virological Methods 149:269-276 (2008).*
Tang et al. Highly sensitive TaqMan RT-PCR assay for detection and quantification of both lineages of West Nile virus RNA. Journal of Clinical Virology 36:177-182 (2006).*
REPLI-g Principle and Procedures [online] [retrieved on Dec. 2, 2014] retrieved from http://www.qiagen.com/us/resources/technologies/wga/replig-principal-procedure/.*
Krokan et al. Uracil in DNA-occurrence, consequences and repair. Oncogene 21:8935-8948. (Year: 2002).*
Mill et al. Whole genome amplification of sodium bisulfite-treated DNA allows the accurate estimate of methylated cytosine density in limited DNA resources. BioTechniques 41:603-607. (Year: 2006).*
Fraga et al., Biotechniques. 33(3):632, 634, 636-49 (2002).
Frommer et al. Proc Natl Acad Sci U S A. 89(5):1827-31 (1992).
Herman et al. Proc Natl Acad Sci U S A. 93(18): 9821-26 (1996).
Laird, Nat Rev Cancer. 2003;3(4):253-66.
Olek et al. Nucleic Acids Research Oxford University Press, Surrey, GB, vol. 24, Nr. 24 2 pgs. (1996).
International Search Report dated Jun. 22, 2009 issued in International Application No. PCT/EP2009/051388 (English Translation).
Written Opinion of the International Search Authority dated Aug. 7, 2010 issued in IUnternational Application No. PCT/EP2009/051388 (English Translation).
International Preliminary Report on Patentability Chapter 1 dated Sep. 7, 2010 issued in nternational Application No. PCT/EP2009/051388 (English Translation).

* cited by examiner

*Primary Examiner* — Samuel C Woolwine
(74) *Attorney, Agent, or Firm* — Ballard Spahr LLP

(57) ABSTRACT

The present invention relates to a reaction mixture for the amplification of nucleic acids, the non-methylated cytosine bases of which have been converted to uracil bases by means of a bisulfition reaction. The invention also discloses methods for amplifying bisulfited nucleic acid and for determining the nucleic acid methylation state, and also kits based on the reaction mixture according to the invention.

8 Claims, 1 Drawing Sheet

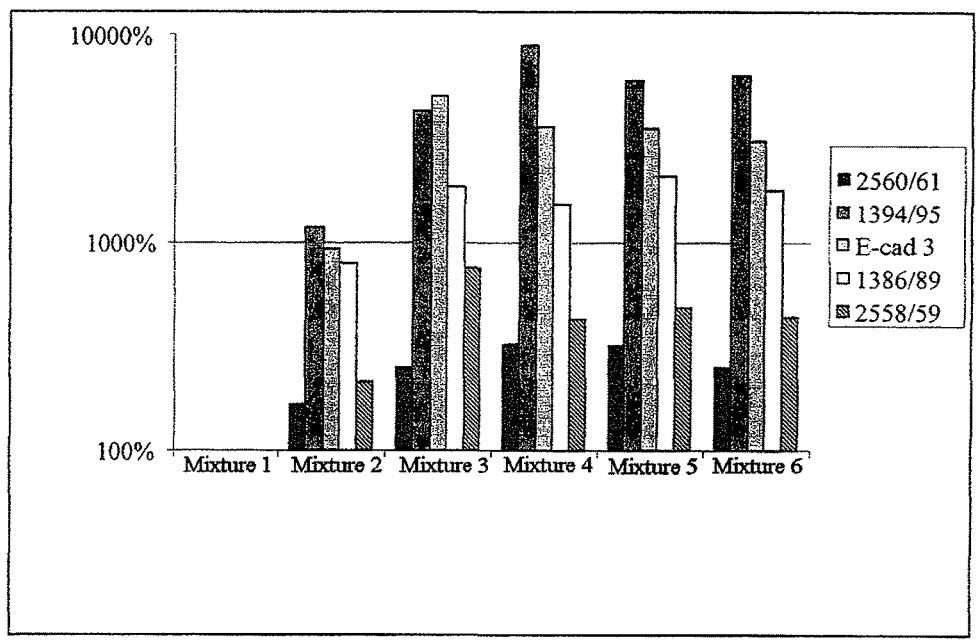

AMPLIFICATION OF BISULFITE-REACTED NUCLEIC ACIDS

CROSS-REFERENCE TO RELATED APPLICATIONS

The present application is a National Phase Application of International Application No. PCT/EP2009/051388, filed Feb. 6, 2009, which claims priority to German Patent Application No. 10 2008 008 313.5 filed Feb. 7, 2008, which applications are incorporated herein fully by this reference.

TECHNICAL FIELD OF THE INVENTION

The present invention is in the field of molecular biology and epigenetics and relates to the amplification of nucleic acids, the non-methylated cytosine bases of which have been converted by means of a bisulfition reaction to uracil bases. Reaction mixtures and kits for the nucleic acid amplification according to the invention and methods for analysing the nucleic acid methylation state are also disclosed.

PRIOR ART

Epigenetic mechanisms cause changes in gene expression which are not accompanied by an alteration of the coding sequence of the genes but which may be passed on, for example by mitosis. In higher eukaryotes, the best studied epigenetic mechanism is DNA methylation, in addition to RNA-associated silencing and histone modification (Serman et al., Coll Antropol. 2006; 30(3):665-71).

DNA is methylated on the cytosine residues of the nucleic acid and preferably on dinucleotides having a cytosine-guanine sequence (CpG). The most important base modification in eukaryotes is methylation at the 5' position of cytosine.

However, the type of methylation may be different, with CNG and asymmetric cytosine methylation in addition to CpG methylation having been disclosed in plants, and a small amount of CT methylation having been detected in Drosophila. Furthermore, a non-CG methylation has been found in various fungal species. Said CpG dinucleotides often accumulate in relatively small (500 bp-4 kb) sections of the nucleic acid and are referred to as CpG islands, if the GC content is >55%. CpG islands are usually found around regulatory regions of genes and may influence transcriptional regulation of said genes. Methylation of the CpG islands in most cases results in inactivation of the affected gene and therefore plays a part in a number of biological processes (imprinting, X-chromosomal inactivation, gene expression), though in particular in the development of benign as well as malignant tumours (Egger et al., Nature. 2004; 429(6990):457-63), in some phenotypes, diseases and in cell ageing.

Analysing nucleic acid methylation is therefore important particularly in diagnostics (for example for early diagnosis and classification of cancer and other diseases), while the targeted modification of the methylation state for the purpose of gene regulation represents a potential therapeutic strategy. Detecting the methylation state of nucleic acids is therefore of high importance.

The methylation state of nucleic acids may be analysed by bisulfition of the latter, which involves non-methylated cytosine bases of said nucleic acids being converted to uracil bases, while methylated cytosine bases remain unchanged. An overview of various techniques for analysing the methylation state of nucleic acids, in particular bisulfition, can be found in Fraga et al., Biotechniques. 2002; 33(3):632, 634, 636-49 and Laird, Nat Rev Cancer. 2003; 3(4):253-66. Depending on the methylation state of the starting nucleic acid, the bisulfition reaction therefore results in nucleic acid sequences having a different sequence, and the methylation state of the starting nucleic acid can then be inferred after analysis of said sequence, inter alia by PCR or by sequencing.

Approx. 5-15% of all cytosine bases are methylated, depending on the developmental state and the physiological condition of the cell. Since the methylated cytosine bases remain unaffected by the bisulfition reaction, this results in approx. 85-95% of all cytosine bases of the starting nucleic acid being converted to uracil bases. Consequently, this provides the starting nucleic acid with a substantially new base composition, with the conversion of cytosine to uracil producing G:U mismatches from G:C base pairs, and therefore the two strands of the nucleic acid being no longer fully complementary to one another from then onwards. The mismatches generated may be considerable because, for example, a DNA containing 5% methylated cytosine with a GC content of 50% may have a GC content of only 28% after bisulfition.

Amplification of this converted nucleic acid with altered base composition obtained after the bisulfition reaction may lead to great difficulties, in particular in the case of PCR amplification. There is therefore a need for an improved amplification of nucleic acids converted by bisulfition. The present invention provides solutions to this problem.

SUMMARY OF THE INVENTION

The present invention relates to improved reaction mixtures and methods for amplifying nucleic acid converted by means of bisulfition, to methods for analysing the nucleic acid methylation state, and to corresponding kits. The present invention is based on the surprising finding that amplification of nucleic acid subjected to conversion by means of a bisulfition reaction can be improved significantly by increasing the concentration of the nucleotides dATP and dTTP over the concentration of dCTP and dGTP in the reaction mixture.

One aspect of the present invention relates to a reaction mixture for nucleic acid amplification, comprising dATP, dTTP, dCTP and dGTP, and nucleic acid comprising uracil, characterized in that the initial concentration of dATP and dTTP is higher than that of dCTP and dGTP.

Particular preference is given to the nucleotides used not being tagged or labelled, i.e. in particular not having any fluorescent, luminescent or weight markers, dye-containing or staining markers (in particular enzyme markers), magnetic, radioactive, radiologically detectable or immunological markers, antigens, lectins or otherwise detectable markers or labels.

In a preferred embodiment, the initial concentration of dATP and dTTP in the reaction mixture is from 200% to 600% of the initial concentration of dCTP and dGTP. In a further preferred embodiment, the initial concentration of dATP and dTTP in the reaction mixture is from 300% to 500% of the initial concentration of dCTP and dGTP.

A second aspect of the present invention relates to a method for amplifying nucleic acid converted by means of a bisulfition reaction, comprising the steps of a. contacting the bisulfited nucleic acid with at least one set of primers, at least one polymerase, and dATP, dTTP, dCTP and dGTP; and b. amplifying the nucleic acid by means of the polymerase, characterized in that the initial concentration of dATP and dTTP is higher than that of dCTP and dGTP. In a preferred embodiment, the initial concentration of dATP and dTTP in the reaction mixture is from 200% to 600% of the initial concentration of dCTP and dGTP. In a further preferred embodiment, the initial concentration of dATP and dTTP in the reaction mixture is from 300% to 500% of the initial concentration of dCTP and dGTP. In a further preferred embodiment, the amplification is carried out isothermally or by means of temperature cycling, with more preference being given to the amplification being an RCA or an MDA.

A further aspect of the present invention relates to a method for analysing the methylation state of nucleic acids, comprising the steps of:
 a. bisulfiting the nucleic acid;
 b. amplifying the bisulfited nucleic acid from step a according to the second aspect of the invention;
 c. detecting the nucleic acid bases converted from cytosine to uracil due to said bisulfition,
wherein each uracil detected corresponds to a non-methylated cytosine present in the original nucleic acid.

A further aspect of the present invention relates to a kit having a reaction mixture as described above. The latter comprises dATP, dTTP, dCTP and dGTP and at least one polymerase and is characterized in that the concentration of dATP and dTTP is higher than that of dCTP and dGTP.

The nucleic acid used in the method or reaction mixture according to the invention is preferably DNA, particularly preferably genomic DNA or mitochondrial DNA.

In a preferred embodiment, the concentration of dATP and dTTP in the kit corresponds to from 200% to 600% of the concentration of dCTP and dGTP, preferably from 300% to 500% of the concentration of dCTP and dGTP.

The reaction mixture or method according to the invention may be used in particular for amplifying complex nucleic acid mixtures. While the labelling reactions mentioned at the outset can be used only up to a complexity of around $10^3$ nucleotides, the reaction mixture according to the invention or a method carried out using said reaction mixture is suitable for nucleic acids to be amplified which have a complexity of $\geq 10^4$ nucleotides, preferably $\geq 10^5$, particularly preferably $\geq 10^6$ and very particularly preferably $\geq 10^7$ nucleotides, up to a maximum of $10^{11}$.

Further embodiments of the invention arise from the claims, the detailed description and the examples.

BRIEF DESCRIPTION OF THE DRAWINGS

FIG. 1 depicts the increase in sequence representation based on the Ct values determined by means of real-time PCR (Table 1). A difference of one Ct cycle corresponds to a 2-fold difference.

DETAILED DESCRIPTION OF THE INVENTION

Nucleic acid methylation is a post-replicative, epigenetic mechanism which is of considerable importance for gene regulation in eukaryotes. In the methylation reaction, the addition of a methyl group to carbon atom no. 5 of the pyrimidine base of cytosine results in the formation of 5-methyl cytosine. This methyl addition is catalysed in vivo by transferring the methyl group of S-adenosyl methionine (methyl donor) to cytosine (methyl acceptor) with the aid of DNA methylases (DNMTs) and takes place preferably in cytosines located 5' of a guanine (CpG).

CpG dinucleotides are under-represented in the genome due to evolutionary mechanisms and to the tendency of methyl cytosine to deaminate spontaneously. They are accumulated, however, in particular in the regulatory regions of genes as "CpG islands" which are from approx. 500 bp-4 kb in size and have a GC content of >55%. These CpG islands contain approximately 20% of all CpG dinucleotides and are associated with the regulatory regions of approximately half of all genes of the particular genome. In general, genes having a high transcriptional activity are located in non-methylated genomic regions. In contrast, genes having only low transcriptional activity or no activity at all are located in methylated regions.

Since the methylation of DNA may lead to physiological changes in, for example, DNA packing density, expression or inactivation of genes, and since changes in the methylation pattern have been associated in particular with the development of cancer, some genetic diseases and cell ageing, the targeted alteration/correction of the methylation state is considered to be employed therapeutically for the purpose of gene regulation. A reliable analysis of the methylation state is absolutely required in particular for this but also for diagnostic applications, for example.

Bisulfition, for example with subsequent amplification/sequencing, which was first described by Frommer et al. (Proc Natl Acad Sci USA. 1992; 89(5):1827-31) has proved suitable for analysing the methylation state of nucleic acids, in particular the methylation status of specific CpG sites.

The present invention provides improved reaction mixtures and methods for amplifying nucleic acid converted by means of bisulfition, methods for analysing the nucleic acid methylation state, and corresponding kits.

Definitions

The term "nucleic acid", as used herein, refers to a ribonucleic acid, preferably a deoxyribonucleic acid, which may be of natural origin, i.e. it may have been obtained inter alia from organisms, tissues, cells or biopsies, or else has been prepared by other methods, inter alia by enzymatic or chemical in vitro reactions. Nucleic acid here also means a modified form of nucleic acid, comprising inter alia thioester bonds rather than phosphoester bonds, base or deoxyribose modifications, for example by attaching organic or inorganic groups, or introduced base analogues (also non-purine or non-pyrimidine analogues). In a preferred embodiment, the nucleic acid is a DNA (deoxyribonucleic acid), a PNA or a cDNA, and more preferably is a genomic or mitochondrial DNA. The nucleic acid may be single-stranded, double-stranded or multi-stranded.

The term "converted nucleic acid" or "converted DNA", as used herein, refers to a nucleic acid or DNA, the composition of which with regard to the relative proportions of A, G, C or T to one another has been changed. Preferably, said term means the conversion of non-methylated cytosines to uracil by bisulfition of said nucleic acid. More preferably, it means the conversion of most or all non-methylated cytosines to uracil by bisulfition of said nucleic acid such that at least 50%, preferably more than 75%, particularly preferably more than 90%, of the non-methylated cytosines have been converted to uracil. A nucleic acid converted by means of bisulfition reaction is also referred to as "bisulfited". Since bisulfition converts the non-methylated cytosines to uracil, a converted nucleic acid contains at least one uracil, if originally at least one non-methylated cytosine had been present. Furthermore, since only the cytosines but not the guanines of the complementary strand are converted, conversion results in a nucleic acid with a G:C ratio of the complementary strands that does not equal 1, i.e. the DNA no longer conforms to Chargaff's rule of base ratios. Furthermore, there may be various variants of a converted nucleic acid which depend on the number of non-methylated cytosines of this nucleic acid. For example, a nucleic acid containing 2 cytosines may accordingly result in 4 different variants after bisulfition, depending on the methylation state of said cytosines, since none, the first, the second or both of said cytosines may be non-methylated and is/are converted to uracil. These different variants may be detected by means of specific primers or sets of primers. Either purified nucleic acid or lysates may be converted.

The term "amplification", as used herein, refers to the propagation of a nucleic acid (template or matrix nucleic acid) by at least a factor of 2. Preferred methods for amplifying nucleic acids are global amplification methods which amplify the entire converted nucleic acid of a sample. These include isothermal and non-isothermal whole genome amplification (WGA) methods. Two amplification methods which are particularly preferred for the purpose of the present invention are RCA (rolling circle amplification) and MDA (multiple displacement amplification).

RCA is based on rolling circle replication which occurs inter alia with many viruses (see, for example, Baker, T. A. & Kornberg, A. (1992) DNA Replication; Freeman, N.Y.). RCA generally comprises multiple rounds of an isothermally conducted, enzymatically catalysed nucleic acid strand synthesis, with a polymerase extending a primer hybridized to a circular nucleic acid to give a nucleic acid strand, while continuously progressing on said circular nucleic acid (the target circle). This method, first described by Fire et al. (Proc. Natl. Acad. Sci. USA. (1995); 92(10):4641-5), is characterized by linear kinetics, easy scalability, the use of a multiplicity of possible polymerases (unlike PCR, no heat-stable polymerase is required), and high specificity and sensitivity, and can therefore be utilized for reliably and reproducibly duplicating nucleic acids up to the milligram range. RCA may also be used for exponentially duplicating nucleic acid. This is achieved by means of at least two primers, or a set of primers, wherein said primers hybridize with at least two binding sites on the target circle or else hybridize with at least one binding site on the target circle and at least one binding site on the complementary strand. An overview of RCA can be found in Demidov, V. (2005) Encyclopedia of Diagnostic Genomics and Proteomics; Marcel Dekker, Inc.; 1175-1179.

MDA, which is likewise carried out isothermally and which has the same advantages of RCA, as stated above, comprises amplifying a linear nucleic acid, for example genomic DNA, by hybridization of primers and by means of a polymerase, with the nucleic acid strands formed being utilized simultaneously for in each case secondary hybridizing of said primers, i.e. secondary rounds of amplification being initiated on primary amplification products. For RCA, as well as MDA, preference is given to employing highly productive polymerases with strand-displacement activity and with or without 3'→5' exonuclease proofreading activity, which can replicate up to 100 kb of the nucleic acid in high quality, without falling off the nucleic acid template. A preferred example of such a polymerase is Phi29 DNA polymerase. Owing to using a heat-labile polymerase and carrying out the reaction at a constant temperature, an amplification carried out in this way has multiple advantages over the amplification by means of PCR, for example. Thus the polymerase used may be heat-inactivated after the amplification reaction in order to prevent said polymerase from degrading the amplification product. Furthermore, due to the reaction being carried out at a constant low temperature, no aerosol containing the amplicons is formed that could contaminate neighbouring reactions. Furthermore, the simultaneous use of exonuclease-resistant random primers enables the complete genome to be amplified in an extremely uniform manner, virtually without being affected by the nucleic acid sequence of the template (whole genome amplification; WGA). An overview of MDA and applications in WGA can be found, inter alia, in Dean et al. (Proc. Natl. Acad. Sci. USA (2002);99(8):5261-6).

In a particularly preferred embodiment of the invention, WGA by means of MDA employs the REPLI-g® Kit (QIAGEN), which involves, after chemical denaturization and neutralization of the template nucleic acid, amplification in the presence of Phi-29 DNA polymerase and exonuclease-resistant random primers at 30° C. and for approximately 8 to 10 hours or overnight. The average length of the product generated in a WGA by means of the REPLI-g® Kit is typically greater than 10 kb and is within a range from approximately 2 kb to 100 kb.

Further linear and exponential amplification methods suitable for the present invention are familiar to the skilled worker, inter alia PCR (polymerase chain reaction), LCR (ligase chain reaction), NASBA (nucleic acid sequence based amplification), SDA (strand displacement amplification), TMA (transcription-mediated amplification), 3SR (self-sustained sequence replication), LAMP (loop-mediated amplification), HDA (helicase-dependent amplification), RPA (recombinase-polymerase amplification).

The term "primer", as used herein, refers to a molecule which serves as a start site for an enzyme having nucleic acid-polymerase or nucleic acid-ligase activity. A primer may be a protein, a nucleic acid or another molecule which is deemed suitable as polymerase or ligase start site by the skilled worker. Said molecule may serve as a start site due to intermolecular or else intramolecular interaction. Preference is given to nucleic acid primers. They may hybridize over their entire length with the template nucleic acid or may to some extent have mismatches, and usually are from 4 to 30 nucleotides (nt) in length. The primers may contain a random sequence or a degenerate sequence such that said primers may hybridize to many different sequences of the nucleic acid converted by means of bisulfition. In other cases, the primer may contain a sequence such that said primer can hybridize only to one or a few particular sequences in the nucleic acid converted by means of bisulfition. The primers are between 4 and 100 nt, preferably between 5 and 50 nt, and very particularly preferably between 6 and 25 nt in length.

The term "set of primers", as used herein, refers to a group of primers which is required for carrying out an amplification and which consists of at least one primer. For linear amplifications, a set of primers consists of at least one primer. For exponential amplifications, a set of primers likewise consists of at least one primer, if the latter hybridizes to at least two different positions of the template nucleic acid, thereby exponentially amplifying the nucleic acid section between the hybridization positions. Preferably, the set of primers for exponential amplifications consists of at least two primers, however, which hybridize to two different positions of the template nucleic acid (primer pair); here too, the nucleic acid section between the hybridization positions is exponentially amplified.

The term "corresponding sets of primers", as used herein, refers to at least two sets of primers which are specific for the in each case non-bisulfited variant and for at least one bisulfited variant of the nucleic acid.

The term "polymerase", as used herein, refers to an enzyme which catalyses the formation of phosphodiester bonds between individual nucleotides within a nucleic acid strand (e.g. DNA and RNA polymerases). Particular preference is given to employing in the amplification method according to the invention polymerases suitable for amplification reactions, in particular all DNA polymerases. Polymerases can be divided into heat-labile or heat-stable enzymes. Preferred polymerases include polymerases having the enzyme number EC 2.7.7.7, Taq polymerase, polymerases with proofreading activity, polymerases with strand displacement activity, mutated polymerase, as well as polymerases containing accessory factors (e.g. helicase, single-strand binding proteins, recombination proteins) and holoenzymes forming a functional DNA-polymerase complex. In a preferred embodiment, the polymerase is a DNA polymerase, more preferably a Taq polymerase, a DNA polymerase with proofreading activity, or a polymerase with strand displacement activity. Strand displacement activity is a property of a polymerase, by which an "old" strand of a double-stranded nucleic acid is displaced from the other "old" strand (strand displacement) during the polymerase reaction. Strand displacement polymerases include all polymerases capable of carrying out strand displacement. These include enzymes such as, for example, Phi29 DNA polymerase, Klenow exo minus DNA polymerase, Vent DNA polymerase, Deep Vent™ DNA polymerase, Bst DNA polymerase, 9oNm™ DNA polymerase and Bca DNA polymerase.

Strand displacement polymerases may also be present in a mutated form, for example as "exo minus" variants (i.e. without exonuclease activity). These include polymerases such as Phi29 DNA polymerase, Klenow exo minus DNA polymerase. Other suitable polymerases are Taq DNA polymerase and Tth DNA polymerase.

In principle, said polymerases may also be in a modified form. This includes truncated variants or those variants which have mutations compared to the respective wild types. Said mutations may be mutations which influence, for example enhance, the functionality of the polymerases, or else mutations that do not influence the functionality of said polymerases, for example due to conservative substitution.

Such conservative substitutions comprise variations in which an amino acid is replaced with another amino acid from the following group:

| Group | Type | Amino acids |
| --- | --- | --- |
| 1. | Small aliphatic, non-polar or slightly polar residues | Ala, Ser, Thr, Pro and Gly |
| 2. | Polar, negatively charge residues and their amides | Asp, Asn, Glu and Gln |
| 3. | Polar, positively charged residues | His, Arg and Lys |
| 4. | Large aliphatic, non-polar residues | Met, Leu, Ile, Val and Cys |
| 5. | Aromatic residues | Phe, Tyr and Trp. |

The following list depicts preferred conservative substitutions of the type mentioned:

| Original residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

Said polymerases may furthermore be chemically modified.

Particularly preferably, the invention provides for the polymerase used being modified so as to have "hot start" properties. Such a polymerase is suitable for use in a "hot start PCR" which differs from the known PCR only by the first step. The polymerase chain reaction here is started only when the reaction mixture has reached the desired maximum temperature. Thereby it is achieved that polymerization starts only when the primers have specifically bound to the DNA sequence, as a result of which fewer artifacts are produced. Preference is given here to three routes of imparting "hot start" properties to a polymerase:

1. Modification by an Antibody:

In this case, an antibody is used which binds reversibly to the polymerase and suppresses the activity of the latter at normal ambient temperature. Since the antibody, unlike the polymerase, is not thermostable, it denatures and dissociates during the first heating step. The polymerase can then start working.

2. Chemical Modification:

In this case, the polymerase is reversibly inactivated by a chemical agent, for example formaldehyde or a dicarboxylic anhydride.

3. Competitive Inhibition:

In this case, the polymerase is competitively inhibited, for example by polyanions binding to the active site.

It is also possible to add to the polymerase further accessory factors which improve or enable amplification of the nucleic acid converted by means of bisulfition. Said factors include, for example, helicases, single-stranded DNA binding proteins (e.g. SSB, T4gp32), recombination proteins (e.g. recA, Mut proteins).

The term "ligase", as used herein, refers to a ligase which links ("ligates") two nucleic acid strands by generating a phosphorus ester bond. It includes DNA and RNA ligases. Thus, "ligase" refers to an enzyme having the enzyme number EC 6.5.1.1, EC 6.5.1.2 or EC 6.5.1.3.

The term "initial concentration", as used herein, refers to the concentration of the particular substance present at the start of the amplification of the nucleic acid. For example, the initial concentration of dATP, dTTP, dCTP and/or dGTP (dNTPs) refers to the concentration of the particular deoxyribonucleoside triphosphate at the start of the amplification of the converted nucleic acid, for example at the start of an MDA. Since the converted nucleic acid which is used as template for said amplification contains a different amount of the individual nucleotides (A, T, C, G, U), the concentration of said dNTPs decreases at a different rate during amplification, i.e. as a function of the frequency of the in each case complementary nucleotide of the converted nucleic acid.

The term "methylation state", as used herein, refers to the presence or absence of methylation of the individual cytosine bases of a nucleic acid in question. Determining the methylation state of a nucleic acid, for example according to the methods of the present invention, therefore identifies those cytosines of the nucleic acid in question which were present in methylated or non-methylated form.

Bisulfition Reaction and Determination of the Methylation Status

The methylation status of a nucleic acid may be determined in different ways. A method known to the skilled worker, which is particularly suitable for this, is bisulfition of the nucleic acid by means of sodium bisulfite ($NaHSO_3$), followed by an amplification (e.g. by means of RCA or MDA) of the converted nucleic acid for the purpose of determining the converted cytosines or the unconverted 5-methylcytosines. Said determination may be carried out, inter alia, by means of sequencing or else either purely qualitatively or quantitatively by using various sets of primers which are specific for converted or unconverted nucleic acid regions (complementary sets of primers).

The bisulfition reaction described by Frommer et al. (Proc Natl Acad Sci USA. 1992; 89(5):1827-31) comprises incubating DNA which has been denatured to single strands in a mixture of 3.1 M sodium bisulfite and 0.5 mM hydroquinone at pH 5.0 and 50° C. for 16 to 40 h in order to convert the non-methylated cytosines to uracil. Upon completion of the bisulfition reaction, excess sodium bisulfite is removed by means of dialysis prior to further usage of the converted nucleic acid.

Another option for carrying out the bisulfition reaction is the EpiTect® Bisulfite Kit (available from QIAGEN) which allows a bisulfition reaction under controlled conditions that avoid fragmentation of the nucleic acid, and convenient purification of the converted nucleic acid.

Conversion and purification of the converted nucleic acid are usually followed by at least one amplification step, by means of which the converted nucleic acid is propagated in order to enable the converted cytosines to be detected. In a preferred embodiment, amplification is carried out by means of RCA or MDA, more preferably by using the REPLI-g® Kit. However, a multiplicity of other suitable amplification and detection methods are known to the skilled worker. Reference is made here, by way of example, to bisulfite genomic sequencing (BGS), described by Frommer et al. (Proc Natl Acad Sci USA. 1992; 89(5):1827-31), or methylation-specific PCR (MSP), described by Herman et al. (Proc Natl Acad Sci USA. 1996; 93(18): 9821-26). While BGS involves sequencing the converted DNA by means of standardized methods (e.g. chain termination methods) after amplification and cloning thereof into a vector, MSP is based on providing at least one set of primers (forward and reverse primers) which is specific for the methylated and thus unconverted, or the non-methylated and converted nucleic acid sequence. When using two sets of primers (in each case specific for the converted or unconverted nucleic acid) for each nucleic acid position of interest, the presence of the methylated or non-methylated state can then be determined specifically for each nucleic acid position of interest by means of amplification via formation of an amplicon.

Reaction Mixture for Amplification by Means of Bisulfition of Converted Nucleic Acid, Method for Amplification (and Analysis of the Methylation State) of Converted Nucleic Acid The reaction mixture provided by the present invention for nucleic acid amplification is based on the surprising finding that amplification of nucleic acid subjected to conversion by means of a bisulfition reaction can be improved significantly by increasing the concentration of the nucleotides dATP and dTTP over the concentration of dCTP and dGTP in the reaction mixture.

A first aspect of the present invention relates to a reaction mixture for nucleic acid amplification, comprising dATP, dTTP, dCTP and dGTP, and nucleic acid containing uracil, wherein the initial concentration of dATP and dTTP is higher than that of dCTP and dGTP. In one embodiment, the reaction mixture furthermore comprises a ligase.

A second aspect of the present invention relates to a method for amplifying nucleic acid converted by means of a bisulfition reaction, using the reaction mixture according to the invention and comprising the steps of
   a. contacting the bisulfited nucleic acid with at least one set of primers, at least one polymerase, and dATP, dTTP, dCTP and dGTP, wherein the initial concentration of dATP and dTTP is higher than that of dCTP and dGTP; and
   b. amplifying said nucleic acid by means of said polymerase.

In a preferred embodiment of the invention, amplification is carried out by means of MDA or RCA, more preferably by using the REPLI-g® Kit.

In a further preferred embodiment, amplification of the nucleic acid is carried out in the presence of a ligase.

The appropriate conditions for carrying out an amplification of nucleic acid, for example by means of MDA or RCA, are sufficiently known to a skilled worker, as is the fact that said conditions can be and should be adjusted to the particular properties of said nucleic acid in order to ensure optimal amplification. Thus, for example, the reaction temperature may be adjusted to the primer pairs and/or polymerase(s) used during an MDA or RCA. Likewise the annealing time and/or annealing temperature during a PCR may be varied as a function of the nucleic acid to be amplified. Equally, it is possible to employ different polymerases, buffers or starting concentrations of the nucleotides or of the nucleic acid to be amplified.

A third aspect of the present invention relates to a method for analysing the methylation state of nucleic acid, comprising the steps of
   a. bisulfiting the nucleic acid;
   b. amplifying the bisulfited nucleic acid from step a according to the second aspect of the invention, i.e. by using the reaction mixture according to the invention,
   c. detecting the nucleic acid bases converted from cytosine to uracil due to said bisulfition,
wherein each uracil detected corresponds to a non-methylated cytosine present in the original nucleic acid.

In a preferred embodiment of the reaction mixture and of the method of the present invention, the initial concentration of dATP is the same as that of dTTP, and the initial concentration of dCTP is the same as that of dGTP. In a further preferred embodiment, the initial concentration of dATP and dTTP is more than 500% of the initial concentration of dCTP and dGTP. In a further preferred embodiment, the initial concentration of dATP and dTTP is from 200% to 600% of the initial concentration of dCTP and dGTP; more preferably, the initial concentration of dATP and dTTP is from 300% to 500% of the initial concentration of dCTP and dGTP. In a further preferred embodiment, the initial concentration of dATP and dTTP is 300%, 400% or 500% of the initial concentration of dCTP and dGTP. In a further preferred embodiment, the initial concentration of dCTP and dGTP in the reaction mixture is 20-3000 µM, 50-2000 µM or 100-1000 µM.

In a preferred embodiment of the reaction mixture and of the method of the present invention, the polymerase is a DNA polymerase, more preferably a Taq polymerase, a DNA polymerase with proofreading activity, or a polymerase with strand displacement activity. More preferably, the polymerase is selected from the group consisting of Phi29 DNA polymerase, Klenow exo minus DNA polymerase, Vent™ DNA polymerase, Deep Vent™ DNA polymerase, Bst DNA polymerase, 9oNm™ DNA polymerase, Bca DNA polymerase, and exo minus variants thereof. In a further preferred embodiment, further accessory factors are added to the polymerase, which enhance or enable amplification of the nucleic acid converted by means of bisulfition.

In a further embodiment of the reaction mixture and of the second aspect of the present invention, the nucleic acid is a nucleic acid converted by means of bisulfition, which preferably comprises essentially no non-methylated cytosine bases, more preferably no non-methylated cytosine base. This also applies to the nucleic acid resulting from step a of the third aspect of the invention. In a further embodiment, the G:C ratio of the complementary strands of the nucleic acid does not equal 1 and/or the complementary strands of the nucleic acid are not fully complementary to one another. In a preferred embodiment, the complementary strands of the nucleic acid are 1-10%, 10-20%, 20-30%, 30-40%, 40-50%, 50-60%, 60-70%, 70-80%, 80-90%, 90-99.9%, or between (not including) 50 and 100%, 75 and 100%, or 90 and 100%, complementary to one another.

In a further preferred embodiment of the reaction mixture and of the method of the present invention, the nucleic acid is selected from the group consisting of DNA, PNA, genomic DNA, mitochondrial DNA and cDNA. More preferably, the nucleic acid is mitochondrial or genomic DNA. In a further preferred embodiment, the nucleic acid is single-stranded.

In a further embodiment of the reaction mixture and of the method of the present invention, said reaction mixture furthermore comprises at least one set of primers. In a preferred embodiment, the reaction mixture has at least two corresponding sets of primers which are specific for in each case the methylated and therefore unconverted variant of the nucleic acid or for at least one non-methylated and therefore converted variant of the nucleic acid. In a further preferred embodiment, the at least one set of primers or the at least two corresponding sets of primers is/are specific for at least one CpG island nucleic acid sequence and/or located in at least one regulatory region of at least one gene (e.g. a promoter).

CpG islands are genomic regions having a statistically increased CpG dinucleotide density. Said density is based on the single nucleotide and dinucleotide frequencies within the entire genome section in question. CpG means cytosine-phosphatidyl-guanosine. The letter p is also stated in order to better distinguish GC from CG in phosphonucleoside chains (=DNA molecules) (see also 5' end, 3' end). CpG islands are defined as DNA sections of from 0.5 kb to 2 kb in length which have an increased GC content of more than 60%, with the CG content of the total genome being at 40%. CpG islands are generated by mechanisms involved in the utilization of genetic material as information carrier. As a result, CpG islands are important labels which are of importance, for example, for genetics, medicine and bioinformatics.

In a further preferred embodiment, the at least one set of primers or the at least two corresponding sets of primers is/are specific for at least one nucleic acid sequence comprising at least one CpG island. In a further preferred embodiment, the at least one set of primers or the at least two corresponding sets of primers is/are specific for at least one CpG island nucleic acid sequence, the methylation state of which is associated with a phenotype. The reaction mixture preferably comprises between 5 and 10, 10 and 20, 20 and 50, 50 and 100, 100 and 250, or more than 250, sets of primers, corresponding sets of primers, or random primers. In a further preferred embodiment, at least one, preferably half, more preferably all, of these sets of primers is/are specific for a CpG island nucleic acid sequence, the methylation state of which is associated with a disease.

In a further embodiment of the reaction mixture and of the method of the present invention, the reaction mixture furthermore comprises an amplification buffer. The compositions of such buffers are sufficiently well-known to the skilled worker.

In a further embodiment of the method according to the invention an additional step of denaturing the nucleic acid is carried out prior to the bisulfition reaction. In a preferred embodiment, said denaturation is carried out reversibly and/or thermally and/or under alkaline conditions. In a further embodiment, the disulfition reaction is followed by an additional step of purifying the converted nucleic acid. In a preferred embodiment, said purification is carried out by means of dialysis or precipitation. In a further embodiment, the nucleic acid is amplified in a linear or exponential, preferably exponential, manner.

In a further embodiment of the method according to the invention for analysing the methylation state of nucleic acid, bisulfition of the nucleic acid is carried out using the above-described method by Frommer et al., preferably by using the QIAGEN EpiTect® Kit. In a further embodiment, detection is carried out by means of gel fractionation, Southern blotting, sequencing or RT-PCR.

Kits

The present invention furthermore provides kits for improved amplification of nucleic acid converted by means of bisulfition, and for determining the nucleic acid methylation state.

In one embodiment, the kit according to the invention comprises dATP, dTTP, dCTP, dGTP and at least one polymerase, wherein the concentration of dATP and dTTP is higher than that of dCTP and dGTP. In a preferred embodiment, the concentration of dATP and dTTP is from 200% to 600% of the concentration of dCTP and dGTP, preferably from 300% to 500% of the concentration of dCTP and dGTP. In a further embodiment, the concentration of dCTP and dGTP is 10 mM. In a further embodiment, the nucleotides are in a lyophilised form which, after reconstitution with solvents, for example water, gives the concentrations and concentration ratios according to the invention.

In a further embodiment, the kit according to the invention furthermore comprises at least one set of primers. In a preferred embodiment, the kit comprises at least two corresponding sets of primers which are specific for in each case the methylated and therefore unconverted variant of the nucleic acid or for at least one non-methylated and therefore converted variant of said nucleic acid. In a further preferred embodiment, the at least one set of primers or the at least two corresponding sets of primers is/are specific for at least one CpG island nucleic acid sequence and/or located in at least one regulatory region of at least one gene (e.g. a promoter). In a further preferred embodiment, the at least one set of primers or the at least two corresponding sets of primers is/are specific for at least one nucleic acid sequence comprising at least one CpG island. In a further preferred embodiment, the at least one set of primers or the at least two corresponding sets of primers is/are specific for at least one CpG island nucleic acid sequence, the methylation state of which is associated with a phenotype. The reaction mixture preferably comprises between 5 and 10, 10 and 20, 20 and 50, 50 and 100, 100 and 250, or more than 250, sets of primers, corresponding sets of primers, or random primers. In a further preferred embodiment, at least one, preferably half, more preferably all, of these sets of primers is/are specific for a CpG island nucleic acid sequence, the methylation state of which is associated with a disease. In a further embodiment, the kit according to the invention comprises a polymerase in the presence of a ligase.

In a preferred embodiment, the polymerase is a DNA polymerase, more preferably a Taq polymerase, a DNA polymerase with proofreading activity, or a polymerase with strand displacement activity. More preferably, the polymerase is selected from the group consisting of Phi29 DNA polymerase, Klenow exo minus DNA polymerase, Vent™ DNA polymerase, Deep Vent™ DNA polymerase, Bst DNA polymerase, 9oNm™ DNA polymerase, Bca DNA polymerase, and exo minus variants thereof. In a further preferred embodiment, further accessory factors are added to the polymerase, which enhance or enable amplification of the nucleic acid converted by means of bisulfition.

EXAMPLES

Example 1

Genomic DNA was obtained from human blood with the aid of the QIAamp method (QIAGEN) according to a standard protocol. 1 µm of the DNA obtained in this way was used for a bisulfition reaction (conversion reaction) using the EpiTect Kit (QIAGEN) according to a standard protocol. 5 µl of the purified converted DNA were used for a whole genome amplification. To this end, the REPLI-g Kit (QIAGEN) was employed, with 29 µl of the REPLI-g Midi reaction buffer, 2 µl of the REPLI-g Midi polymerase (Phi29 polymerase) and different volumes of a mix of 10 mM dATP and dTTP being added to 5 µl of the purified converted DNA. The initial concentration of dGTP and dCTP was constantly fixed to 1 mM.

TABLE 1

Volumes of the dATP/dTTP mix which were added to the REPLI-g reactions and the initial concentrations resulting therefrom in the mixture

| | | dATP | dTTP | dGTP | dCTP |
|---|---|---|---|---|---|
| Mixture 1 | 0 µl dATP/dTTP | 1 mM | 1 mM | 1 mM | 1 mM |
| Mixture 2 | 1 µl dATP/dTTP | 1.24 mM | 1.24 mM | 1 mM | 1 mM |
| Mixture 3 | 2 µl dATP/dTTP | 1.48 mM | 1.48 mM | 1 mM | 1 mM |
| Mixture 4 | 3 µl dATP/dTTP | 1.73 mM | 1.73 mM | 1 mM | 1 mM |
| Mixture 5 | 4 µl dATP/dTTP | 1.97 mM | 1.97 mM | 1 mM | 1 mM |
| Mixture 6 | 5 µl dATP/dTTP | 2.22 mM | 2.22 mM | 1 mM | 1 mM |

The total volume of the reaction mixture was 41 µl. The reaction was incubated at 30° C. for 8 hours. After incubation, the reaction was stopped by incubating at 65° C. for 5 mM. The DNA produced was quantified by means of PicoGreen (Invitrogen). 10 ng of the amplified DNA were analysed by means of real time PCR for bisulfited genomic sequences. Real time PCR was carried out by means of QuantiTect SybrGreen reagents (QIAGEN) according to a standard protocol.

The following primer pairs were used for real time PCR using the QuantiTect SybrGreen Kit (QIAGEN):

```
2560/61:
GTGATGGTGGGTATGGGTTAGAAGGATTTT
and

CAACTCATTATAAAAAATATAATACCAAA

1393/94:
CCCCTTCTAAAAACTCCCCAA
and

TGTAGGGGAATTGGAATTAGGT

Ecad3:
TGGTTGTAGTTATGTATTTATTTTTAGTGGTGTT
and

ACACCAAATACAATCAAATCAAACCAAA

1386/89:
GAGAGAGAAGTAGTTGTGTA
and

CCATTCTATCTCCAATAACACCCT

2558/59:
GGATTTGATTGATTATTTTATGAAGATTTTTAT
and

CCATACCCAAAAAAAAAACTAAAAAAATACC
```

Table 2 shows the Ct values determined for the various primer pairs by means of real time PCR. The Ct value (threshold cycle) corresponds to the cycle of the PCR in which fluorescence increases for the first time significantly above background fluorescence. With the same initial amount of template DNA, a lower Ct value thus corresponds to a more effective PCR.

TABLE 2

Ct values determined by means of real time PCR

| | 2560/61 | 1393/94 | E-cad 3 | 1386/89 | 2558/59 |
|---|---|---|---|---|---|
| Mixture 1 | 28.89 | 31.07 | 31.65 | 32.40 | 34.26 |
| Mixture 2 | 28.2 | 27.50 | 28.4 | 29.42 | 33.18 |
| Mixture 3 | 27.58 | 25.65 | 26.00 | 28.18 | 31.36 |
| Mixture 4 | 27.19 | 24.59 | 26.47 | 28.46 | 32.16 |
| Mixture 5 | 27.2 | 25.16 | 26.5 | 28.01 | 31.99 |
| Mixture 6 | 27.59 | 25.07 | 26.70 | 28.22 | 32.14 |

As the results indicate, the Ct values for an amplification of nucleic acid subjected to conversion by a bisulfition reaction are significantly lowered by increasing the initial concentration of the nucleotides dATP and dTTP in the reaction mixture over the initial concentration of dCTP and dGTP, corresponding to an improved and more effective PCR. This applies to all primer combinations tested and particularly to mixtures 3 to 6, i.e. with an increase in the initial concentration of the nucleotides dATP and dTTP in the reaction mixture over the initial concentration of dCTP and dGTP of approximately 50%-120%.

FIG. 1 shows the increase in sequence representation based on the Ct values determined, with a difference of one Ct cycle corresponding to a 2-fold difference. Here too there is a clear indication that increasing the initial concentration of the nucleotides dATP and dTTP in the reaction mixture over the initial concentration of dCTP and dGTP resulted in a significant improvement of the amplification of the bisulfited nucleic acid, for all primer combinations tested.

Example 2

Genomic DNA was obtained from human blood with the aid of the QIAamp method (QIAGEN) according to a standard protocol. 1 µg of the DNA obtained in this way was used for a bisulfition reaction (conversion reaction) using the EpiTect Kit (QIAGEN) according to a standard protocol. 5 µl of the purified converted DNA were used for a whole genome amplification. To this end, the REPLI-g Kit (QIAGEN) was employed, with 29 µl of the REPLI-g Midi reaction buffer, 1 µl of the REPLI-g Midi polymerase (Phi29 polymerase) and different volumes of a mix of 5 mM dATP and dTTP being added to 5 µl of the purified converted DNA. The initial concentration of dGTP and dCTP was constantly fixed to 0.24 mM.

TABLE 3

Volumes of the dATP/dTTP mix which were added to the REPLI-g reactions and the initial concentrations resulting therefrom in the mixture

|  |  | dATP | dTTP | dGTP | dCTP |
|---|---|---|---|---|---|
| Mixture 1 | 0 µl dATP/dTTP | 0.24 mM | 0.24 mM | 0.24 mM | 0.24 mM |
| Mixture 2 | 5 µl dATP/dTTP | 0.83 mM | 0.83 mM | 0.24 mM | 0.24 mM |
| Mixture 3 | 6 µl dATP/dTTP | 0.95 mM | 0.95 mM | 0.24 mM | 0.24 mM |
| Mixture 4 | 7 µl dATP/dTTP | 1.07 mM | 1.07 mM | 0.24 mM | 0.24 mM |
| Mixture 5 | 8 µl dATP/dTTP | 1.19 mM | 1.19 mM | 0.24 mM | 0.24 mM |
| Mixture 6 | 9 µl dATP/dTTP | 1.31 mM | 1.31 mM | 0.24 mM | 0.24 mM |

The total volume of the reaction mixture was 41 µl. The reaction was incubated at 30° C. for 8 hours. After incubation, the reaction was stopped by incubating at 65° C. for 5 min. The DNA produced was quantified by means of PicoGreen (Invitrogen). 10 ng of the amplified DNA were analysed by means of real time PCR for bisulfited genomic sequences. Real time PCR was carried out by means of QuantiTect SybrGreen reagents (QIAGEN) according to a standard protocol.

The following primer pairs were used for real time PCR using the QuantiTect SybrGreen Kit (QIAGEN):

```
699bis:
GGTAGGGATTTGTGATATTGT
and

AATACCATAACACATAACCTAA

1386/89:
GAGAGAGAAGTAGTTGTGTA
and

CCATTCTATCTCCAATAACACCCT

C3:
GGAGTGGAGGAAATTGAGAT
and

CCACACAACAAATACTCAAAAC
```

Table 4 shows the Ct values determined for the various primer pairs by means of real time PCR. The Ct value (threshold cycle) corresponds to the cycle of the PCR in which fluorescence increases for the first time significantly above background fluorescence. With the same initial amount of template DNA, a lower Ct value thus corresponds to a more effective PCR.

TABLE 4

Ct values determined by means of real time PCR

|  | 699bis | 1386/89 | C3 |
|---|---|---|---|
| Mixture 1 | 30.21 | 30.76 | 31.43 |
| Mixture 2 | 27.41 | 28.11 | 28.47 |
| Mixture 3 | 26.35 | 29.34 | 28.90 |
| Mixture 4 | 26.98 | 28.87 | 29.01 |
| Mixture 5 | 25.54 | 27.92 | 28.04 |
| Mixture 6 | 26.18 | 29.34 | 28.17 |

As the results indicate, the Ct values for an amplification of nucleic acid subjected to conversion by a bisulfition reaction are significantly lowered by increasing the initial concentration of the nucleotides dATP and dTTP in the reaction mixture over the initial concentration of dCTP and dGTP, corresponding to an improved and more effective PCR. This applies to all primer combinations tested and particularly to mixtures 2 to 6, i.e. with an increase in the initial concentration of the nucleotides dATP and dTTP in the reaction mixture over the initial concentration of dCTP and dGTP of approximately 350%-550%.

The invention claimed is:

1. A method for amplifying a bisulfite treated deoxyribose nucleic acid, comprising:
   a) contacting a bisulfite treated deoxyribose nucleic acid with at least one set of primers, at least one polymerase, dATP, dTTP, dCTP and dGTP, wherein the percent of the initial concentration of dATP and dTTP is 300% to 500% more than the initial concentration of dCTP and dGTP; and
   b) amplifying, with at least one polymerase, the bisulfite treated deoxyribose nucleic acid, wherein amplifying is carried out is carried out isothermally.

2. The method of claim 1, wherein the bisulfite treated deoxyribose nucleic acid is contacted with at least one set of primers complementary to at least a portion of the sequence of the deoxyribose nucleic acid prior to bisulfite treatment or at least one set of primers complementary to at least a portion of the sequence of the bisulfite treated deoxyribose nucleic acid.

3. The method of claim 2, wherein at least one set of primers is specific for at least one CpG island nucleic acid sequence, wherein the methylation state of the CpG island nucleic acid sequence is associated with a phenotype or a disease.

4. The method of claim 2, wherein the bisulfite treated deoxyribose nucleic acid is contacted with between 5 and 250 sets of primers.

5. The method of claim 2, wherein the bisulfite treated deoxyribose nucleic acid is contacted with more than 250 sets of primers.

6. The method of claim 1, wherein the bisulfite treated deoxyribose nucleic acid is amplified in the presence of a ligase.

7. The method of claim 1, wherein amplifying comprises RCA, MDA, or SDA.

8. The method of claim 1, wherein the deoxyribose nucleic acid is genomic DNA or mitochondrial DNA.

* * * * *